Figure 1:
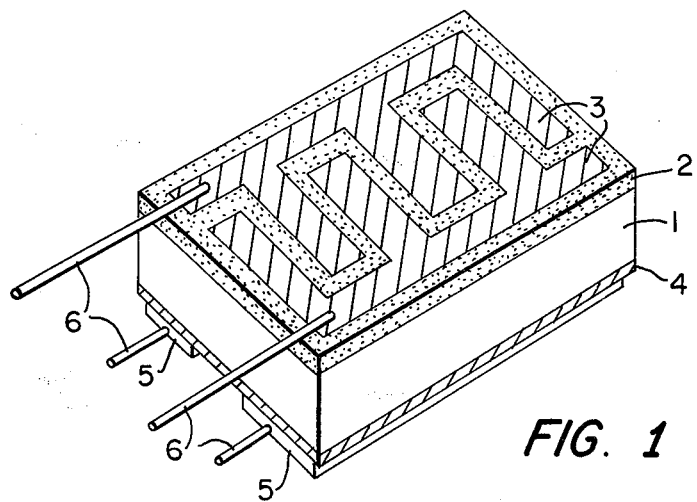

United States Patent [19]

Nakatani et al.

[11] 4,241,019
[45] Dec. 23, 1980

[54] COMBUSTIBLE GAS DETECTING ELEMENT

[75] Inventors: Yoshihiko Nakatani, Osaka; Seiichi Nakatani, Kadoma; Masayuki Sakai, Katano; Michio Matsuoka, Ibaragi, all of Japan

[73] Assignee: Matsushita Electric Industrial Co., Ltd., Japan

[21] Appl. No.: 12,557

[22] Filed: Feb. 15, 1979

[30] Foreign Application Priority Data

Feb. 20, 1978 [JP] Japan .................................. 53/18948

[51] Int. Cl.$^3$ ........................................... G01N 27/12
[52] U.S. Cl. .................... 422/94; 73/27 R; 324/71 SN; 338/34; 422/98
[58] Field of Search ............................. 338/34, 22 SD; 324/71 SN; 73/27 R; 23/232 E; 422/94–98; 252/519

[56] References Cited

U.S. PATENT DOCUMENTS 3,999,947  12/1976  Mihara et al. .......................... 422/95
4,045,178  8/1977  Okinada et al. ........................ 422/98

FOREIGN PATENT DOCUMENTS 49-5480  2/1974  Japan ......................................... 422/98
51-63693  6/1976  Japan ......................................... 422/98

OTHER PUBLICATIONS

Moeller, "Inorganic Chemistry–An Advanced Textbook", John Wiley & Sons, Inc., New York, 1952, p. 754.

Primary Examiner—Arnold Turk
Attorney, Agent, or Firm—Wenderoth, Lind & Ponack

[57] ABSTRACT

Combustible gas detecting element for detecting the concentration of a combustible gas such as isobutane, ethane, propane and hydrogen. It comprises $\gamma\text{-}Fe_2O_3$, $\gamma\text{-}Al_2O_3$ and at least one of La, Ce, Pr and Nd in terms of $La_2O_3$, $Ce_2O_3$, $Pr_2O_3$ and $Nd_2O_3$, respectively. This gas detecting element is an improvement over $\gamma\text{-}Fe_2O_3$, and is advantageous for its highly stable load life even under severe conditions of a high temperature and a high humidity and for its high sensitivity to a combustible gas.

2 Claims, 2 Drawing Figures

U.S. Patent

Dec. 23, 1980

4,241,019

COMBUSTIBLE GAS DETECTING ELEMENT

This invention relates to a combustible gas detecting element for detecting a combustible gas by being changed in its resistivity upon being subjected to a combustible gas, namely a reducing gas, and provides such an element having a long stable life under actual operation even in a high humidity atmosphere.

Recently, various metal oxide semiconductors were studied and suggested for gas detecting elements. However, conventional gas detecting elements are not completely satisfactory for actual social demands. For example, some do not change their resistivity very much upon being brought into contact with a gas, that is they are not very sensitive to a change of concentration of gas. Some other conventional elements are not satisfactory as to their stability to resistivity for long term use under voltage application and/or high humidity. The stability, more specifically insensitivity, of gas detecting elements to humidity is very much required because they are often used in a very humid atmosphere such as in kitchens and bath rooms.

It was recently found that gamma-type ferric oxide ($\gamma$-$Fe_2O_3$) having a spinel-type crystalline structure has excellent gas detection characteristics. There are various crystalline structures of ferric oxides which are very different from each other in their chemical and physical properties. Among them, the best known one is alpha-type ferric oxide ($\alpha$-$Fe_2O_3$) having a corundum-type crystalline structure. Besides, $\gamma$-$Fe_2O_3$, $\beta$-$Fe_2O_3$, $\delta$-$Fe_2O_3$, etc. are known. Among them, only the $\gamma$-$Fe_2O_3$ has actually useful gas detection characteristics.

The sensitivity of this $\gamma$-$Fe_2O_3$ to a reducing gas, namely a combustible gas, is most remarkable when it has a temperature between 300° and 400° C., and is known to have highest sensitivity at about 350° C., which sensitivity is usually defined by the ratio of Ra (its resistance in air) to Rg (its resistance in the gas to be detected). A more important factor for a gas detecting element is the change rate of resistance of the element unit concentration of gas in a gas concentration range in which the gas detection should be performed. This change rate of resistance will be called hereinafter "resistance change ratio". The resistance change ratio is required to be as large as possible. This resistance change ratio determined by how quantitatively the gas concentration can be detected in the gas concentration for the gas detection. In order to realize a gas detecting element of high performance and high reliability, not only the sensitivity but also the resistance change ratio of the element is required to be constant for a long time even under severe operational conditions.

Further, usually an aging process is employed for producing gas detecting elements. However, it is desired to avoid the necessity for such an aging process in view of its productivity and its cost. In order to remove the aging process, the produced gas detecting element is required to have stable properties for a long time from just after the production. However, conventional gas detecting elements were not satisfactory as to these points.

Accordingly, it is an object of this invention to provide a combustible gas detecting element which has a large resistance change ratio and can detect gas concentration highly quantitatively, and which keeps its initial properties stably for a long time even under severe conditions such as high temperature and high humidity.

This object is achieved according to this invention by providing a combustible gas detecting element comprising 99.0 to 25 mole percent of gamma-type ferric oxide ($\gamma$-$Fe_2O_3$), 0.5 to 70 mole percent of gamma-type aluminum oxide ($\gamma$-$Al_2O_3$), and 0.05 to 15 mole percent, in total, of at least one member selected from the group consisting of lanthanum (La), cerium (Ce), praseodymium (Pr) and neodymium (Nd) which are in terms of $La_2O_3$, $Ce_2O_3$, $Pr_2O_3$ and $Nd_2O_3$, respectively.

Figure 2:
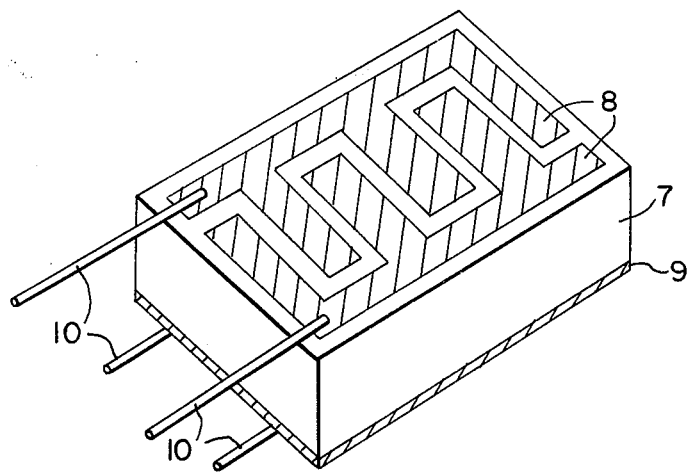

This invention will be more detailedly described hereinafter with the aid of drawings, in which:

FIG. 1 is a perspective view of an example of a gas detecting element of this invention in the form of a sintered film; and FIG. 2 is a perspective view of an example of a gas detecting element of this invention in the form of a sintered body.

According to this invention, by using $\gamma$-$Fe_2O_3$ and $\gamma$-$Al_2O_3$ and adding various additives thereto, a gas detecting element having a large resistance change ratio and capable of highly quantitatively detecting gas concentration and of keeping its properties for a long time even under severe conditions such as high temperature and high humidity can be realized.

Hereinafter, this invention will be described by using Examples with reference to FIGS. 1 and 2.

EXAMPLE 1

Various compositional ratios of mixtures of $Fe_3O_4$ (having an average particle size of 0.3 micron), $\gamma$-$Al_2O_3$ and $Nd_2O_3$ were employed in amounts listed in Table 1. Each of the thus prepared mixtures was wet-milled by using stainless steel pot with stainless balls, and was then pulverized. The thus made mixture was dried in vacuum at a temperature of 80° C., and was then sintered in vacuum at a temperature of 800° C. for 1 hour. Polyethyleneglycol was added to the thus made sintered mixture to make a paste.

Meanwhile, an alumina substrate 1, having a width of 5 mm and a breadth of 5 mm and a thickness of 0.5 mm, for supporting a gas detecting element was prepared. On the alumina substrate 1, the above prepared paste was printed in a thickness of about 70 microns, and was dried in air at room temperature. Then, the paste-applied substrate was sintered at a temperature 400° C. for 1 hour in air, whereby a gas detecting element 2 was made. On the element 2, comb-type electrodes 3 were formed by vacuum-evaporating gold, with the distance between the electrodes being 0.5 mm. On the opposite surface of the substrate was applied a commercially available glaze resistor paste of ruthenium oxide, and the paste was sintered to form a glaze resistor 4 as a heater. On the heater 4 were printed gold electrodes 5, and these electrodes were sintered as electrodes for the heater. Lead wires 6 were bonded to the electrodes 3 and 5 by means of conductive paste.

At this stage, the starting $Fe_3O_4$ had been oxidized to $\gamma$-$Fe_2O_3$, and solvents in the pastes had been evaporated off, whereby a sintered film 2 having practically sufficient mechanical strength was obtained. The thickness of the thus made gas detecting element 2 was about 50 microns.

By using the thus made various gas detecting elements, gas detection measurements were carried out. The temperature of each of the elements for measurements was controlled by controlling the current to flow in the heater 4. The resistance (Ra) of the element in air was measured in a container of 50 liters in which dry air was slowly stirred in a manner not to produce turbulent air flow. The resistance (Rg) of the element in a gas was measured in the above container by introducing an isobutane gas of higher than 99% purity into the container at a rate of 10 ppm/sec in terms of volume percent. The resistance (Rg) was measured at two points, when the introduced gas got to 0.05 volume percent and 0.5 volume percent, respectively, as Rg(0.05) and Rg(0.5), respectively. The reason why the volume percents of 0.05 and 0.5 were selected is because the lower explosion limit (LEL) of isobutane is about 2 volume percent, and thus a combustible gas detecting element is required to detect a gas in the range of from about one fiftieth to about one fifth of the LEL value, from a practical point of view. The gas detection characteristics of each element were measured with the element being kept at a temperature of 350° C. by applying a current to the heater thereof.

In this type of gas detecting elements, the resistance (Rg) of the element is substantially proportional to $C^{-n}$ (where C is the gas concentration of the gas to be detected) in such a concentration range as of 0.05–0.5 volume percent. Therefore, the above-mentioned resistance change ratio can be evaluated by this constant n (which will hereinafter be called concentration factor). For example, when the resistance change ratio is 6.02, n=0.780.

Thereafter, each element was subjected to load life test. That is, current was applied to the heater of each element to keep the element at a temperature of 350° C. and 10 V of d.c. voltage was applied between the electrodes 3. These conditions were kept, where the element was placed in ambient atmosphere of a temperature of 60° C. and a relative humidity of 95 RH%. At two time points (20 hours and 2000 hours) after the start of the application of the above current and the d.c. voltage, each element was subjected to the measurements of gas detection characteristics. Table 1 shows the thus measured initial values Rg, n, and change rates ΔRg, Δn.

As apparent from the above experimental results, the gas detecting element according to this invention comprising 0.5 to 70 mole percent of $\gamma$-$Al_2O_3$, 0.5 to 15 mole percent of $Nd_2O_3$ and the remainder of $\gamma$-$Fe_2O_3$ has a very large resistance change ratio in the practical gas concentration range for detection, and can highly quantitatively detect the gas. Moreover, its gas detection characteristics are stable for a long time from just after the production of the element, even under severe conditions such as a temperature of 60° C. and a relative humidity of 95 RH%. Therefore, the gas detecting element of this invention is not necessary to be subjected to usual aging process.

Hereinabove, $\gamma$-$Al_2O_3$ and $Nd_2O_3$ have been exemplified as additives to $\gamma$-$Fe_2O_3$. However, similar results can be obtained when $Nd_2O_3$ is replaced by $La_2O_3$, $Ce_2O_3$ or $Pr_2O_3$. In such case also, the effective compositional ratio between one of them and $\gamma$-$Al_2O_3$ and $\gamma$-$Fe_2O_3$ coincides with that of the case of using $Nd_2O_3$. That is, when $\gamma$-$Al_2O_3$ is less than 0.5 mole percent or when $Nd_2O_3$, $La_2O_3$, $Ce_2O_3$ or $Pr_2O_3$ is less than 0.05 mole percent, the effect of these additive additions is not significant for obtaining a gas detecting element having a highly stable gas detection characteristics over a long term load life test under high temperature and high humidity. Likewise, when the amount of $\gamma$-$Al_2O_3$ is more than 70 mole percent, the resistance of the gas detecting element becomes abnormaly high both where the element is in the form of a sintered body and in a form of a sintered film, and furthermore, the element does not have sufficient mechanical strength. When the amount of $Nd_2O_3$, $La_2O_3$, $Ce_2O_3$ or $Pr_2O_3$ is more than 15 mole percent, the resultant gas detecting element does not have a sufficiently long life under a high temperature and a high humidity.

In this Example 1, the single use of one of $Nd_2O_3$, $La_2O_3$, $Ce_2O_3$ and $Pr_2O_3$ has been described. However, similar results can be obtained when two, three or all of these additive elements are combined for use as additives to $\gamma$-$Al_2O_3$ and $\gamma$-$Fe_2O_3$, if these combined additives are, in total, in an amount of from 0.05 to 15 mole percent. Details of such combined additives will be exemplified in the following Example 2.

EXAMPLE 2

70 mole percent of a $Fe_3O_4$ powder (having an average particle size of 0.5 micron), 25 mole percent of $\gamma$-$Al_2O_3$ powder and 5 mole percent, in total, of at least one of $La_2O_3$, $Ce_2O_3$, $Pr_2O_3$ and $Nd_2O_3$ (in various combinations) were mixed, wet-milled and pulverized in the same manner as in Example 1 to obtain various mixtures as listed in Table 2. Each mixture was dried in vacuum at a temperature of 80° C. Each of the thus obtained mixture powders was pressure-molded to a rectangular parallelopiped form, and was sintered in nitrogen atmosphere at 800° C. for 1 hour. It was then furnace-cooled to room temperature, and was then again gradually heated to 400° C. in air, and kept at 400° C. for 1 hour, whereby the mixture material was oxidized. At this stage, $Fe_3O_4$ becomes $\gamma$-$Fe_2O_3$.

On the thus made sintered body 7 gold was vacuum evaporated to form a pair of comb electrodes 8. On the opposite surface of the sintered body 7 a platinum heater 9 was bonded by using an inorganic adhesive. Lead wires 10 were bonded to the the comb electrodes 8 and the heater 9 by using a conductive paste. The operational temperature of each gas detecting element was controlled by controlling the electric current applied to the heater 9. Thereby, the element temperature was kept at 350° C., and measurements of gas detection characteristics of the gas detecting elements above prepared were carried out under the same conditions as used in Example 1. Thereafter, the gas detecting elements were placed in an atmosphere of 60° C. and 95 RH% for 2000 hours, with the element temperature being kept at 350° C. After this load life test, each gas detecting element was taken out of the atmosphere, and was subjected to the measurement of gas detection characteristics. These measured characteristics were compared with the above initially measured characteristics. The results of these measured characteristics are shown in Table 2. As apparent from Table 2, the gas detecting elements obtained in this Example 2 have very good load life properties under a high temperature and a high humidity, just as in the case of Example 1.

In Example 1, the form of the gas detecting element mainly shown therein is a sintered film. On the other hand, it is a sintered body in Example 2. As apparent from the foregoing, in both cases, very good results can be obtained as to initial properties and load life properties under severe conditions of a high temperature and a high humidity, although the absolute values of resistances vary from the sintered film form to the sintered body form.

In the above Examples, a glaze heater of ruthenium oxide or a platinum heater was exemplified as a heater.

However, other heaters can also be used, such as a coil type heater. Further, in the above Examples, La, Ce, Pr and Nd were added in the form of oxides. However, any other form of the compounds can be used. For example, they can be added in the form of carbides, if the carbides can be converted to the corresponding oxides upon being heated to a high temperature. Further, in the above Examples, the starting material for the gamma-ferric oxide was $Fe_3O_4$. However, any other starting material therefor can be used, if they can become $\gamma$-$Fe_2O_3$ in the resultant gas detecting element.

As apparent from the foregoing, the gas detecting element according to this invention has a large resistance change ratio, namely a large concentration factor. Further, it has an excellent load life properties under high temperature and a high humidity, to which the gas detecting element would be confronted in actual use. Therefore, the initial properties of the gas detecting element can be kept for a long time e.g. at a place directly exposed to sunshine, such as a kitchen and a bathroom where the humidity is very high, and other similar places.

Further, if necessary, other additives which are not exemplified in the above Examples can be used if the effects obtained by the above exemplified gas detecting elements are not damaged thereby. Further, the gas detecting element of this invention is effective not only to isobutane but also to other combustible gases such as ethane, propane and hydrogen, although only isobutane has been used for the showing.

TABLE 1

| Sample No. | Compositional ratio (mole %) | | | Initial value | | | Change rate of properties after load life test | | | |
|---|---|---|---|---|---|---|---|---|---|---|
| | | | | | | | after 20 hours | | after 2000 hours | |
| | $\gamma$-$Fe_2O_3$ | $\gamma$-$Al_2O_3$ | $Nd_2O_3$ | Ra (KΩ) | Rg(0.5) (KΩ) | on | ΔRg(0.5) (%) | Δn (%) | ΔRg(0.5) (%) | Δn (%) |
| 1* | 100.0 | 0 | 0 | 640 | 31 | 0.59 | −3.4 | −4.2 | +38.2 | −17.3 |
| 2* | 90.0 | 10.0 | 0 | 692 | 34 | 0.74 | +10.6 | −1.0 | +24.6 | −12.4 |
| 3* | 95.0 | 0 | 5.0 | 648 | 32 | 0.60 | −4.1 | −6.3 | +27.4 | −10.7 |
| 4* | 99.9 | 0.1 | 0.01 | 643 | 30 | 0.61 | −3.2 | −5.7 | +38.1 | −16.8 |
| 5 | 99.45 | 0.5 | 0.05 | 652 | 32 | 0.68 | −1.1 | −1.1 | +4.3 | −3.2 |
| 6* | 98.99 | 1.0 | 0.01 | 680 | 34 | 0.63 | +3.4 | −2.2 | +11.4 | −11.6 |
| 7* | 94.9 | 0.1 | 5.0 | 648 | 33 | 0.59 | −2.7 | −2.1 | +20.3 | −9.7 |
| 8 | 90.0 | 5.0 | 5.0 | 684 | 36 | 0.69 | +2.6 | −1.4 | +3.5 | −4.8 |
| 9 | 85.0 | 10.0 | 5.0 | 693 | 37 | 0.76 | +2.7 | −0.9 | +3.0 | −4.1 |
| 10 | 75.0 | 20.0 | 5.0 | 815 | 39 | 0.77 | +0.8 | −0.5 | +2.1 | −0.7 |
| 11 | 45.0 | 50.0 | 5.0 | 887 | 41 | 0.70 | +0.8 | −1.9 | +3.1 | −2.0 |
| 12 | 15.0 | 70.0 | 15.0 | 1247 | 58 | 0.68 | +4.3 | −4.0 | +4.8 | −4.9 |
| 13* | 20.0 | 75.0 | 5.0 | 3400 | 194 | 0.55 | +4.8 | −5.1 | +6.2 | −9.8 |
| 14 | 79.5 | 20.0 | 0.5 | 810 | 41 | 0.77 | +2.9 | ±0 | +3.4 | −0.8 |
| 15 | 79.0 | 20.0 | 1.0 | 813 | 38 | 0.76 | ±0 | −0.7 | +2.8 | −1.1 |
| 16 | 70.0 | 20.0 | 10.0 | 876 | 40 | 0.74 | +3.4 | ±0 | +3.4 | −1.0 |
| 17* | 60.0 | 20.0 | 20.0 | 858 | 48 | 0.64 | +4.2 | −0.9 | +16.9 | −7.8 |

(*samples for comparison)

TABLE 2

| Sample No. | Compositional ratio (mole %) | | | | | Ra (KΩ) | Rg(0.5) (KΩ) | Rg(0.5) (KΩ) | Resistance change ratio | Concentration factor |
|---|---|---|---|---|---|---|---|---|---|---|
| | $La_2O_3$ | $Ce_2O_3$ | $Pr_2O_3$ | $Nd_2O_3$ | | | | | | |
| 21* | 0 | 0 | 0 | 0 | Initial values | 604 | 193 | 37 | 5.17 | 0.71 |
| | | | | | Values after test | 560 | 206 | 45 | 4.57 | 0.66 |
| 22 | 5.0 | 0 | 0 | 0 | Initial values | 612 | 197 | 33 | 5.94 | 0.77 |
| | | | | | Values after test | 634 | 209 | 35 | 5.91 | 0.77 |
| 23 | 0 | 5.0 | 0 | 0 | Initial values | 889 | 274 | 53 | 5.16 | 0.71 |
| | | | | | Values after test | 861 | 288 | 57 | 5.01 | 0.70 |
| 24 | 0 | 0 | 5.0 | 0 | Initial values | 684 | 201 | 36 | 5.63 | 0.75 |
| | | | | | Values after test | 644 | 213 | 38 | 5.52 | 0.74 |
| 25 | 0 | 0 | 0 | 5.0 | Initial values | 778 | 226 | 39 | 5.81 | 0.76 |
| | | | | | Values after test | 749 | 230 | 40 | 5.78 | 0.76 |
| 26 | 2.5 | 2.5 | 0 | 0 | Initial values | 777 | 231 | 38 | 6.08 | 0.78 |
| | | | | | Values after test | 782 | 233 | 39 | 5.97 | 0.78 |
| 27 | 0 | 2.5 | 2.5 | 0 | Initial values | 807 | 235 | 39 | 6.02 | 0.78 |
| | | | | | Values after test | 809 | 238 | 40 | 5.95 | 0.77 |
| 28 | 0 | 0 | 2.5 | 2.5 | Initial values | 833 | 252 | 40 | 6.30 | 0.80 |
| | | | | | Values after test | 845 | 256 | 41 | 6.24 | 0.79 |
| 29 | 2.5 | 0 | 0 | 2.5 | Initial values | 667 | 208 | 36 | 5.78 | 0.76 |
| | | | | | Values after test | 656 | 201 | 36 | 5.58 | 0.74 |
| 30 | 2.0 | 1.0 | 1.0 | 0 | Initial values | 786 | 233 | 37 | 6.29 | 0.80 |
| | | | | | Values after test | 790 | 235 | 38 | 6.18 | 0.79 |
| 31 | 0 | 2.0 | 2.0 | 1.0 | Initial values | 816 | 239 | 40 | 5.98 | 0.77 |
| | | | | | Values after test | 828 | 239 | 41 | 5.82 | 0.76 |

TABLE 2-continued

| Sample No. | Compositional ratio (mole %) | | | | | Ra (KΩ) | Rg(0.5) (KΩ) | Rg(0.5) (KΩ) | Resistance change ratio | Concentration factor |
|---|---|---|---|---|---|---|---|---|---|---|
| | $La_2O_3$ | $Ce_2O_3$ | $Pr_2O_3$ | $Nd_2O_3$ | | | | | | |
| 32 | 1.0 | 0 | 2.0 | 2.0 | Initial values | 844 | 253 | 41 | 6.17 | 0.79 |
| | | | | | Values after test | 845 | 255 | 42 | 6.07 | 0.78 |
| 33 | 2.0 | 1.0 | 0 | 2.0 | Initial values | 690 | 215 | 37 | 5.81 | 0.76 |
| | | | | | Values after test | 699 | 210 | 37 | 5.67 | 0.75 |
| 34 | 2.0 | 1.0 | 1.0 | 1.0 | Initial values | 843 | 263 | 42 | 6.26 | 0.79 |
| | | | | | Values after test | 856 | 260 | 43 | 6.04 | 0.78 |

(*samples for comparison)
($Al_2O_3$: 25mole% (constant), remainder: $\gamma$-$Fe_2O_3$)

What is claimed is:

1. A combustible gas detecting element comprising 99.0 to 25 mole percent of gamma-ferric oxide ($\gamma$-$Fe_2O_3$), 0.5 to 70 mole percent of gamma-aluminum oxide ($\gamma$-$Al_2O_3$), and 0.05 to 15 mole percent, in total, of at least one member selected from the group consisting of lanthanum (La), cerium (Ce), praseodymium (Pr) and neodymium (Nd) in terms of $La_2O_3$, $Ce_2O_3$, $Pr_2O_3$ and $Nd_2O_3$, respectively.

2. A combustible gas detecting element according to claim 1, which is in the form of a sintered film or a sintered body and which has electrodes applied thereto.

* * * * *